United States Patent
Willi

[11] Patent Number: 5,951,496
[45] Date of Patent: Sep. 14, 1999

[54] GUIDE WIRE AND METHOD OF PRODUCING A GUIDE WIRE

[75] Inventor: Jakob Willi, Höri, Switzerland

[73] Assignee: Schneider (Europe) Gmbh, Switzerland

[21] Appl. No.: 08/837,404

[22] Filed: Apr. 15, 1997

[30] Foreign Application Priority Data

May 3, 1996 [EP] European Pat. Off. .............. 96106958

[51] Int. Cl.⁶ ........................................................ A61B 5/00
[52] U.S. Cl. ............................................................. 600/585
[58] Field of Search ................................... 600/434, 435, 600/433, 585

[56] References Cited

U.S. PATENT DOCUMENTS

| | | | |
|---|---|---|---|
| 33,911 | 5/1861 | Samson et al. .......................... | 128/772 |
| 4,538,622 | 9/1985 | Samson et al. .......................... | 128/772 |
| 4,545,390 | 10/1985 | Leary ....................................... | 128/772 |
| 4,554,929 | 11/1985 | Samson et al. .......................... | 128/772 |
| 4,646,044 | 2/1987 | Kuno et al. .............................. | 335/299 |
| 4,676,249 | 6/1987 | Arenas etal. ............................ | 128/657 |
| 4,721,117 | 1/1988 | Mar et al. ................................ | 128/772 |
| 4,748,986 | 6/1988 | Morrison et al. ........................ | 128/772 |
| 4,757,827 | 7/1988 | Buchbinder et al. .................... | 128/772 |
| 4,763,647 | 8/1988 | Gambale .................................. | 128/657 |
| 4,830,023 | 5/1989 | de Toledo et al. ....................... | 128/772 |
| 4,886,067 | 12/1989 | Palermo .................................. | 128/657 |
| 4,922,924 | 5/1990 | Gambale et al. ........................ | 128/772 |
| 4,934,380 | 6/1990 | de Toledo ................................ | 128/772 |
| 4,966,163 | 10/1990 | Kraus et al. ............................. | 128/772 |
| 5,060,660 | 10/1991 | Gambale et al. ........................ | 128/772 |
| 5,063,935 | 11/1991 | Gambale .................................. | 128/657 |
| 5,067,489 | 11/1991 | Lind ........................................ | 128/772 |
| 5,084,022 | 1/1992 | Claude .................................... | 604/164 |
| 5,109,867 | 5/1992 | Twyford, Jr. et al. .................. | 128/772 |
| 5,131,406 | 7/1992 | Kaltenbach ............................. | 128/772 |
| 5,144,959 | 9/1992 | Gambale et al. ........................ | 128/772 |
| 5,147,317 | 9/1992 | Shank et al. ............................. | 604/164 |
| 5,165,421 | 11/1992 | Fleischhacker et al. ................ | 128/772 |
| 5,174,302 | 12/1992 | Palmer .................................... | 128/772 |
| 5,197,486 | 3/1993 | Frassica .................................. | 128/772 |
| 5,228,453 | 7/1993 | Sepetka ................................... | 128/772 |
| 5,259,393 | 11/1993 | Corso, Jr. et al. ....................... | 128/772 |
| 5,267,574 | 12/1993 | Viera et al. .............................. | 128/772 |
| 5,271,415 | 12/1993 | Foerster et al. ......................... | 128/772 |
| 5,282,478 | 2/1994 | Fleischhaker, Jr. et al. ........... | 128/772 |
| 5,287,858 | 2/1994 | Hammerslag etal. ................... | 128/772 |
| 5,376,083 | 12/1994 | Mische .................................... | 600/585 |
| 5,377,690 | 1/1995 | Berthiaume ............................. | 600/585 |
| 5,415,170 | 5/1995 | Hammerslag et al. ................. | 128/657 |
| 5,429,139 | 7/1995 | Sauter ..................................... | 128/772 |
| 5,520,194 | 5/1996 | Miyata et al. ........................... | 600/585 |
| 5,551,444 | 9/1996 | Finlayson ................................ | 600/585 |
| 5,640,970 | 6/1997 | Arenas .................................... | 600/434 |
| 5,664,580 | 9/1997 | Erickson et al. ........................ | 600/585 |
| 5,666,969 | 9/1997 | Urick et al. ............................. | 600/434 |
| 5,682,894 | 11/1997 | Orr et al. ................................. | 600/585 |

FOREIGN PATENT DOCUMENTS

| | | |
|---|---|---|
| 0318046A2 | 5/1989 | European Pat. Off. . |
| 041927A1 | 3/1991 | European Pat. Off. . |
| 9204072 | 3/1992 | WIPO . |

*Primary Examiner*—Max Hindenburg
*Assistant Examiner*—Charles Marmor, II
*Attorney, Agent, or Firm*—Crompton, Seager & Tufte, LLC

[57] ABSTRACT

The guide wire serves in particular for the percutaneous introduction of a balloon dilation catheter into a blood vessel and has a flexible coil which surrounds a likewise flexible shaft and is produced from at least two coil springs, which are rotated together at a connection location over a plurality of turns and are soldered to one another. For the purpose of connection, at the end to be connected, the two coil springs are each slid onto a centering mold, rotated together and soldered. The centering mold is then removed. The connection location is tubular and internally hollow, so that the flexible shaft can be inserted subsequently.

6 Claims, 5 Drawing Sheets

GUIDE WIRE AND METHOD OF PRODUCING A GUIDE WIRE

BACKGROUND OF THE INVENTION

The applicant claims priority under 35 U.S.C. § 119 based upon European Patent Application No. 96106958.0 filed in the European Patent Office on May 3, 1996. The invention relates to a method of producing a guide wire, in particular for the percutaneous introduction of a balloon dilation catheter into a blood vessel, in which the guide wire has a flexible coil which surrounds a likewise flexible shaft and is produced from at least two coil springs which are rotated together at a connection location over a plurality of turns and are soldered to one another. Moreover, the invention relates to a guide wire, in particular for the percutaneous introduction of a balloon dilation catheter into a blood vessel, having a flexible coil which surrounds a likewise flexible shaft and is produced from at least one distal and one proximal coil spring, which coil springs are rotated together at a connection location over a plurality of turns and are soldered to one another.

Numerous embodiments of guide wires of the type are known in the prior art and are used, in particular, for the percutaneous introduction of a balloon dilation catheter into a blood vessel, in particular a constriction in such a vessel. In order for the guide wire to be suitable for introducing a balloon dilation catheter into a constriction in a blood vessel, it must have, in addition to a high operational reliability, special properties, and in particular it must be controllable and very flexible at the distal end. Moreover, the guide wire should have a region which is visible to X-rays which is comparatively short and sharply defined.

A guide wire of this kind is disclosed, for example, in U.S. Pat. No. 4,748,986. This guide wire has a coil which comprises a distal coil spring which is visible to X-rays and a proximal coil spring. The coil surrounds a shaft which at the distal end is conically tapered and connected to a tip. In order to connect the two coil springs, the latter are rotated together at the ends to be connected over a plurality of turns and are soldered continuously to the shaft and a safety strip. This joining of the coil springs and the soldering represent an extremely complex and, in particular, time-intensive manual operation. Due to the comparatively solid solder region, the guide wire is significantly less flexible at the connection location than in front of and behind this region. As a result, the controllability of the guide wire is impaired. In order to improve the desired properties of the guide wire, it has been proposed in U.S. Pat. No. 5,429,139 to connect the two coil springs by means of a connection coil. After stretching the turns to be connected and inserting the flexible shaft, this comparatively short connection coil is rotated in and soldered. This has the effect, inter alia, that the flexibility of the guide wire is impaired to a lesser extent by the connection location. However, the time required to connect the two coil springs is comparatively high, it being necessary to take into account the extreme fineness of the coil springs to be connected and the high demands placed on the reliability of the connection location.

EP-A-0,419,277 shows a further possibility for connecting two coil springs. This method uses an intermediate piece which has grooves on the outside, onto which grooves the coil-spring ends to be connected are rotated.

Various guide wires are shown in U.S. Pat. Nos. 4,934,380; 5,282,478; and 5,415,170.

All documents cited herein, including the foregoing, are incorporated herein by reference in their entireties for all purposes.

SUMMARY OF THE INVENTION

The invention is based on the object of providing a method and a guide wire for generic applications which permit more rapid production and yet meet the high demands with regard to safety.

The method according to the invention is characterized in that, at the end to be connected, the two coil springs are each slid onto a centering mould, rotated together and soldered, and in that the centering mould is then removed. In the method according to the invention, it is no longer necessary to rotate in the extremely fine connection coil, yet a connection location which is tubular and is comparable to the other regions of the guide wire, particularly with regard to flexibility, is nevertheless provided. The centering mould forms a template which significantly facilitates rotating the two coil springs together and thus makes it possible to work more rapidly but nevertheless reliably. The two coil springs which have been rotated together are aligned with respect to one another by the centering mould and can be soldered simply but precisely. The centering mould prevents the solder from being able to penetrate into the interior of the coil, so that the connection location is smooth and internally hollow following removal of the centering mould. As a result, the coil-spring unit can be preassembled and only put on the flexible shaft in a subsequent operation. Preassembled coil-spring units can thus be kept in stock, which significantly facilitates the organization of assembly.

In accordance with a refinement of the invention, the centering mould is designed such that it does not take to the solder during the soldering of the coil springs and does not become joined thereto. Such a centering mould is preferably made from a suitable titanium alloy, for example from Tynel or NiTi alloy. Such a centering mould is very flexible and it has proven extremely suitable for producing such a connection. Since the solder does not become joined to the centering mould and is flexible, it can be removed following soldering in a very simple and gentle manner.

The guide wire according to invention is characterized in that the connection location is designed to be tubular and, with the exception of the shaft, internally hollow. This guide wire is preferably produced in accordance with the above-mentioned method. It has the particular advantage that, in the region of the connection location, it has largely similar properties to the areas in front of and behind this location. Preferably, the solder is applied such that it does not, or does not significantly, project beyond the outside and the inside of the coil in the region of the connection location. It is thus scarcely possible to distinguish the region of the connection location from the other regions with regard to most properties of the guide wire.

In sum, the invention relates to a method of producing a guide wire, in particular for the percutaneous introduction of a balloon dilation catheter into a blood vessel. The guide wire has a flexible coil which surrounds a likewise flexible shaft and is produced from at least two coil springs which are rotated together at a connection location over a plurality of turns and are soldered to one another. At the end to be connected, the two coil springs are each slid onto a centering mould, rotated together and soldered, and the centering mould is then removed again. The centering mould may be designed such that it does not take to the solder during the soldering of the coil springs and does not become joined thereto. The centering mould may consist of a titanium alloy, preferably nickel-titanium alloy. The alloy may be Tynel. The centering mould may have an external diameter which is essentially equal to the internal diameter of at least one of the coil springs. The turns to be connected may be opened up before being rotated together. The distal coil spring may be made from a material which is visible to X-rays, for example tungsten, and the proximal coil spring may be made from a material which is essentially invisible to X-rays, in particular stainless steel.

The invention also relates to a guide wire, in particular for the percutaneous introduction of a balloon dilation catheter into a blood vessel. The guide wire has a flexible coil which surrounds a likewise flexible shaft and is produced from at least one distal and one proximal coil spring which are rotated together at a connection location over a plurality of turns and are soldered to one another. The connection location is designed to be tubular and, with the exception of the shaft, internally hollow. The solder may not, or may not significantly project beyond the outside and the inside of the coil in the region of the connection location. The distal spiral spring may be produced from a wire which has a smaller diameter than the wire from which the proximal coil spring is produced.

These and other objects, features and advantages of the invention will become readily apparent from the following description with reference to the accompanying drawings which show, diagrammatically and by way of example only, preferred but still illustrative embodiments of the invention.

As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTIONS OF THE DRAWINGS

FIG. 1 diagrammatically shows how two coil springs are rotated together;

FIG. 2 diagrammatically shows two coil-spring ends which have been rotated together;

FIG. 3 diagrammatically shows two coil-spring ends which have been rotated together and soldered;

FIG. 4 diagrammatically shows a section of a guide wire according to the invention; and FIG. 5 diagrammatically shows a section of a guide wire in accordance with a variant.

DETAILED DESCRIPTION OF THE INVENTION

Figure 4:
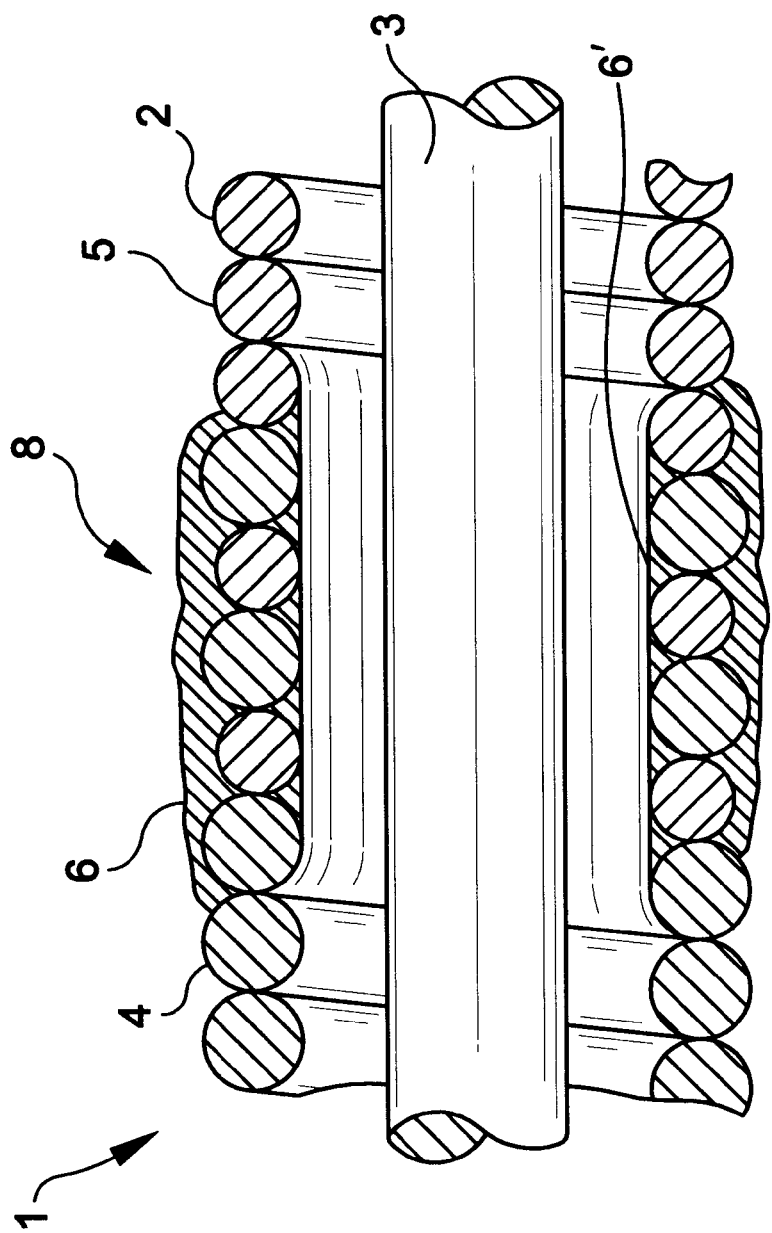

Accordingly, FIG. 4 shows a section of a guide wire 1 which, with the exception of the connection location 8 shown here, may correspond exactly to that of the above-mentioned U.S. Pat. No. 5,429,139. In FIG. 4, the distal end (not shown here) is on the right and the proximal end is on the left. The guide wire 1 has a flexible shaft 3, which at the distal end (not shown here) is tapered and flattened and is fixedly connected to the tip (likewise not shown here). The shaft 3 forms a core wire and is surrounded over its entire length by a likewise flexible coil 2, which has a proximal coil spring 4 and a distal coil spring 5, which are firmly connected to one another at a connection location 8. The coil 4 preferably consists of a rustproof wire having a diameter of, for example, about 0.06 mm. The external diameter C (FIG. 2) of this coil spring 4 is preferably about 0.31–0.32 mm. The distal coil spring 5 is made from a material which is visible to X-rays, for example tungsten, and has an external diameter D of preferably about 0.31 mm. The coil spring 5 is wound from a wire which has a diameter of, for example, about 0.05 mm.

Figure 1:
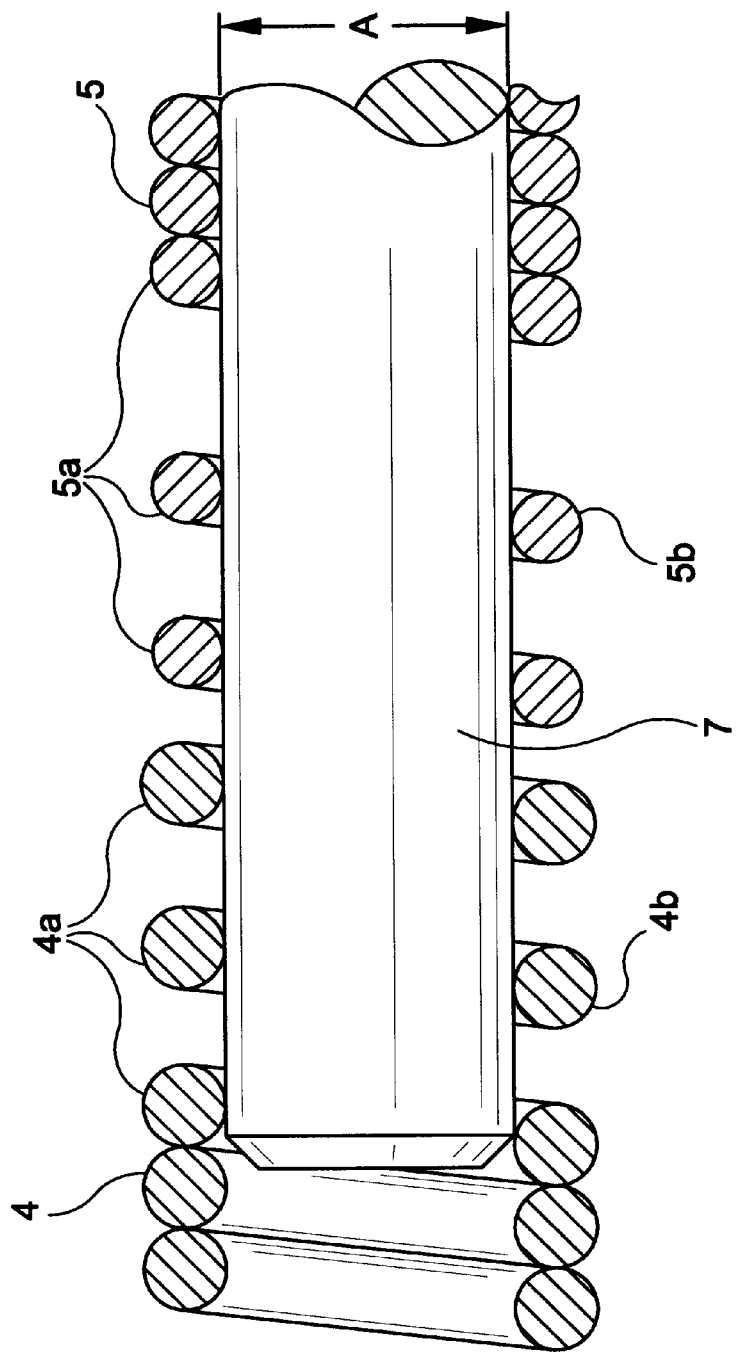

The connection of the two coil springs 4 and 5 is explained in more detail below with reference to FIGS. 1 to 3.

In order to connect the two coil springs 4 and 5 firmly to one another, a few turns, preferably 2 to 5 turns 4a and 5a, are opened up and rotated together at the ends to be connected. In this process, the two coil springs 4 and 5 are preferably pulled onto a centering mould 7. The external diameter A of the centering mould 7 is equal to or slightly less than the internal diameter B of the coil springs 4 and 5. As a result of the guidance of the centering mould, the spirals cannot drift to the side when being rotated together.

Figure 2:
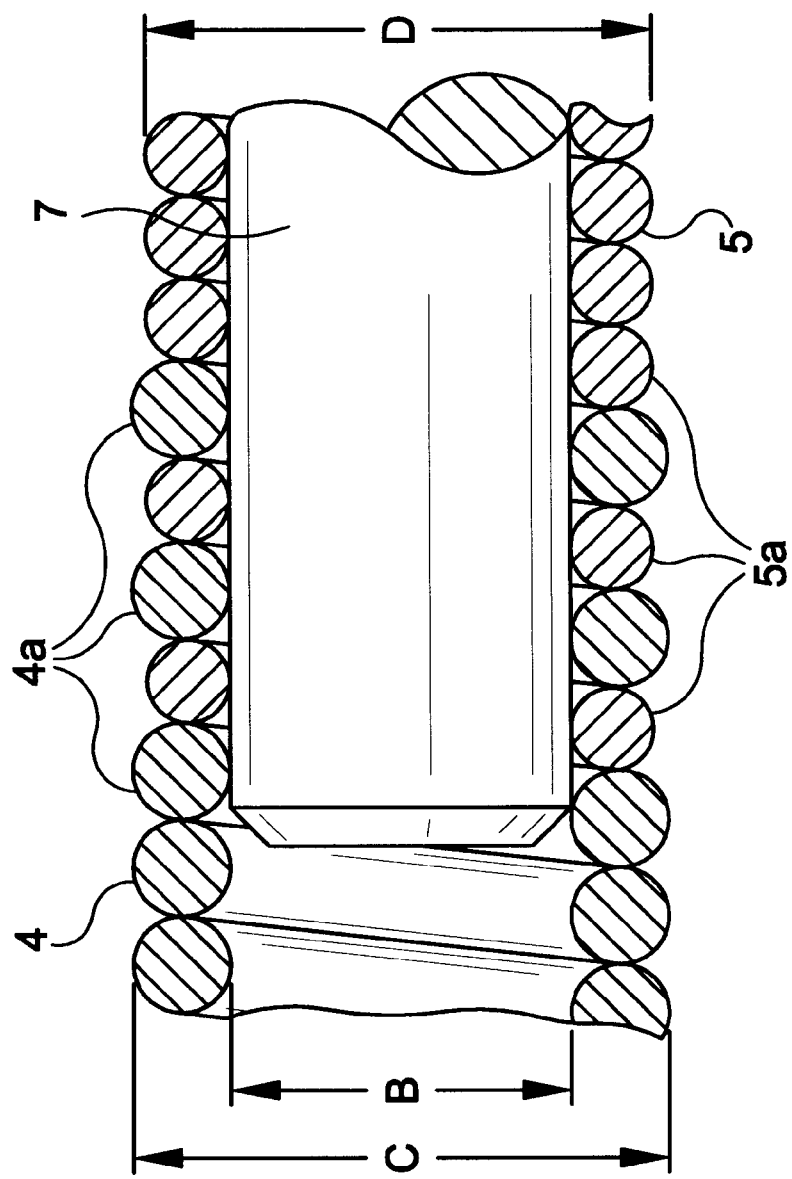
Figure 3:
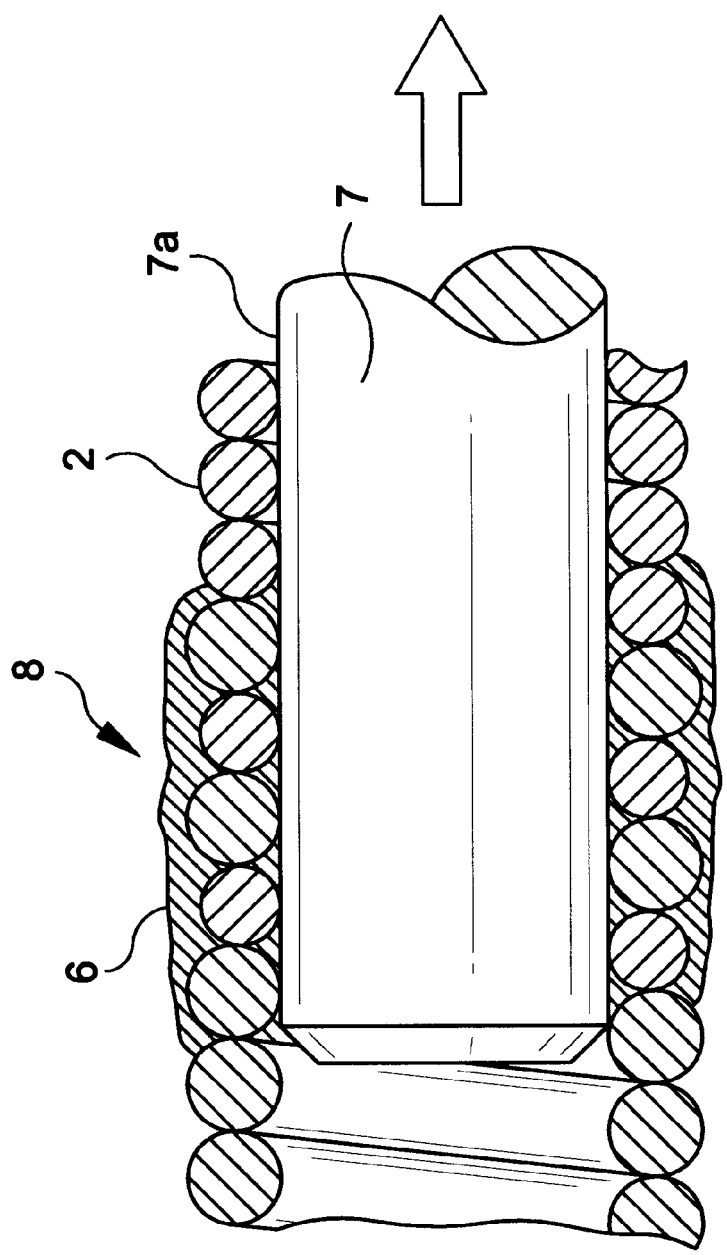

FIG. 2 shows the two coil springs 4 and 5 after the extended turns 4a and 5a have been rotated together. In accordance with FIG. 3, solder 6 is now applied around these turns 4a and 5a. This solder penetrates into the gaps between these turns 4a and 5a and encloses the centering mould 7 on its smooth and cylindrical outside 7a in the region of the turns 4a and 5a. This centering mould 7 is now preferably designed such that it does not take to the solder used and also does not become joined thereto. Preferably, the centering mould consists of a nickel-titanium alloy, for example Tynel or NiTi alloy. However, it is also possible to use other suitable alloys of tungsten or molybdenum. These alloys do not take to the solder 6 and produce a flexible wire and tube piece. After soldering, the centering mould 7 can be pulled out of the coil 2 in a very simple manner without damaging the connection location 8. The two coil springs 4 and 5 are now firmly connected to one another at the connection location 8. The inside 6' of the connection location 8 is smooth and cylindrical, specifically in a manner corresponding to the outside 7a of the centering mould 7. The connection location 8 is likewise cylindrical and essentially does not project beyond the outside of the coil 2.

After the centering mould 7 has been removed, the shaft 3 is inserted into the coil 2 and connected to the tip in a known manner. It is significant that the introduction of the shaft 3 is not impeded by the connection location 8, since the latter is of the same width on the inside as the coil 2 in front of and behind this region. The coil 2 can thus be preassembled without the shaft 3 and be kept in stock.

Figure 5:
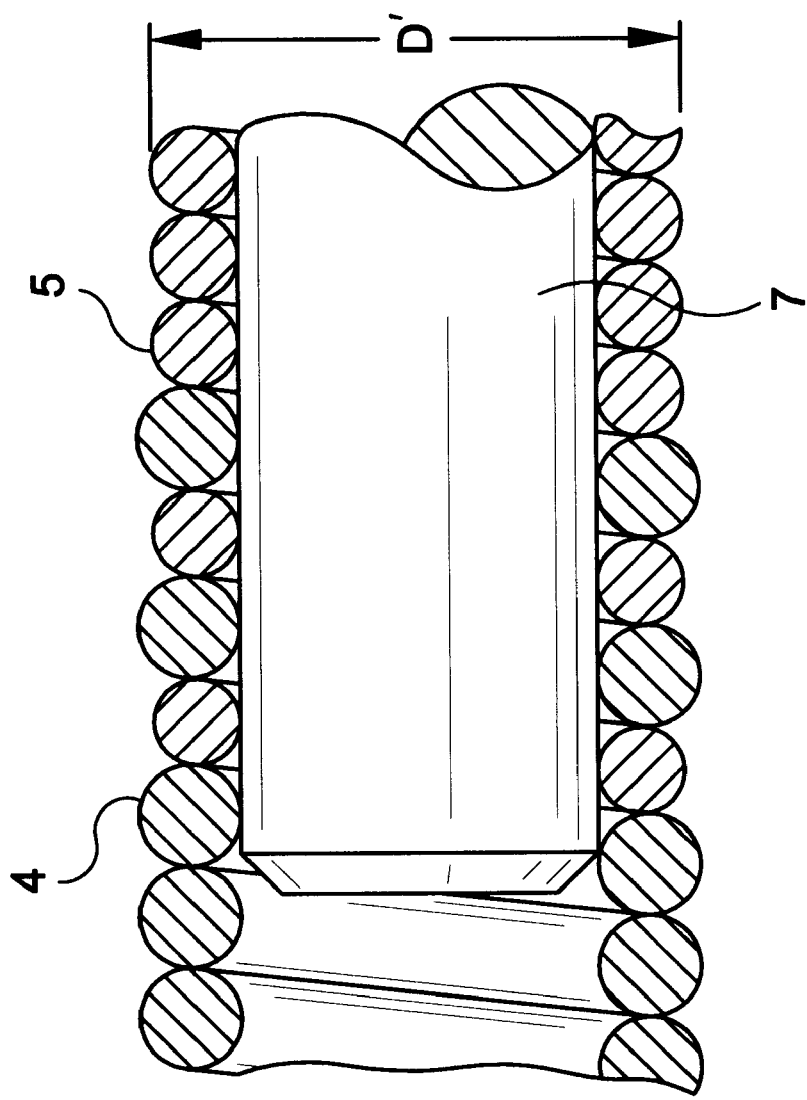

As mentioned above, the distal coil spring 5 is wound from a wire which has a smaller diameter than that of the proximal coil spring 4, as can also be seen from the drawing. In a development of the invention illustrated in FIG. 5, the diameter D' of the distal coil spring 5 is selected to be as large as possible but still such that the outside of the coil spring 5, in the position offset to the side shown here, cannot protrude on the outside, which produces an outside of optimal smoothness in the region of the connection location.

It will be evident from considerations of the foregoing that the guide wire and method for producing a guide wire is now available, and may be constructed using a number of methods and materials, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A guide wire for the percutaneous introduction of a balloon dilation catheter into a blood vessel comprising:

an elongated flexible shaft with an outer diameter, a proximal portion and a distal portion;

a coil spring assembly surrounding and connected to the distal portion of the shaft, the coil spring assembly including a distal coil spring and a proximal coil spring;

the distal coil spring including a proximal end, a distal end, and a plurality of wire turns;

the proximal coil spring including a proximal end, a distal end, and a plurality of wire turns;

the wire turns of the proximal end of the distal coil spring being spaced apart to accommodate the wire turns of the distal end of the proximal coil spring;

the wire turns of the distal end of the proximal coil spring being spaced apart to accommodate the wire turns of the proximal end of the distal coil spring;

the distal end of the proximal coil spring turned into the proximal end of the distal coil spring so that a plurality of the wire turns of the distal end of the proximal coil spring are adjacent to a plurality of the wire turns of the proximal end of the distal coil spring;

a solder joint connecting the distal end of the proximal coil spring to the proximal end of the distal coil spring over a plurality of wire turns;

the solder joint having an inside diameter and an outside diameter; and the inside diameter of the solder joint being larger than the outside diameter of the elongated flexible shaft.

2. The guide wire of claim 1, wherein the distal coil spring consists of a wire which has a smaller diameter than the wire of the proximal coil spring.

3. The guide wire of claim 1, wherein the distal coil spring and the proximal coil spring are comprised of the same material.

4. A guide wire for the percutaneous introduction of a balloon dilation catheter into a blood vessel comprising:

an elongated flexible shaft with an outer diameter, a proximal portion and a distal portion;

a coil spring assembly surrounding and connected to the distal portion of the shaft, the coil spring assembly including a distal coil spring and a proximal coil spring;

the distal coil spring including a proximal end, a distal end, and a plurality of wire turns;

the proximal coil spring including a proximal end, a distal end, and a plurality of wire turns;

the wire turns of the proximal end of the distal coil spring being spaced apart to accommodate the wire turns of the distal end of the proximal coil spring;

the wire turns of the distal end of the proximal coil spring being spaced apart to accommodate the wire turns of the proximal end of the distal coil spring;

the distal end of the proximal coil spring engaging the proximal end of the distal coil spring in a connection area so that at least one turn of the proximal coil spring is positioned between two turns of the distal coil spring;

the proximal end of the distal coil spring being soldered to the distal end of the proximal coil spring in the connection area;

the connection area having an inside diameter and an outside diameter; and the inside diameter of the connection area being larger than the outside diameter of the elongate flexible shaft.

5. The guide wire of claim 4, wherein the distal coil spring consists of a wire which has a smaller diameter than the wire of the proximal coil spring.

6. The guide wire of claim 4, wherein the distal coil spring and the proximal coil spring are comprised of the same material.

* * * * *